US011934909B2

(12) United States Patent
Mongrenier (10) Patent No.: US 11,934,909 B2
(45) Date of Patent: Mar. 19, 2024

(54) DEVICE FOR STORING ELEMENTS, ASSOCIATED INSTALLATION AND ASSOCIATED COMMUNICATION METHOD

(71) Applicant: BIOLOG-ID, Boulogne-Billancourt (FR)

(72) Inventor: Jean-Claude Mongrenier, Aix en Provence (FR)

(73) Assignee: BIOLOG-ID, Boulogne-Billancourt (FR)

( * ) Notice: Subject to any disclaimer, the term of this patent is extended or adjusted under 35 U.S.C. 154(b) by 76 days.

(21) Appl. No.: 17/641,644

(22) PCT Filed: Sep. 8, 2020

(86) PCT No.: PCT/EP2020/075081
§ 371 (c)(1),
(2) Date: Mar. 9, 2022

(87) PCT Pub. No.: WO2021/048127
PCT Pub. Date: Mar. 18, 2021

(65) Prior Publication Data
US 2022/0318531 A1    Oct. 6, 2022

(30) Foreign Application Priority Data
Sep. 10, 2019 (FR) ...................... 1909975

(51) Int. Cl.
*G06K 7/10*      (2006.01)
*H01Q 1/22*      (2006.01)
(Continued)

(52) U.S. Cl.
CPC ....... *G06K 7/10366* (2013.01); *H01Q 1/2216* (2013.01); *H01Q 7/00* (2013.01); *H04B 5/0062* (2013.01)

(58) Field of Classification Search
CPC .... G06K 7/10366; H01Q 1/2216; H01Q 7/00; H01Q 21/061; H04B 5/0062;
(Continued)

(56) References Cited

U.S. PATENT DOCUMENTS 8,770,479 B1 *   7/2014   Shoenfeld .............. G06Q 90/00
                                                235/487
9,653,819 B1 *   5/2017   Izadian .............. H01Q 21/0087
(Continued)

FOREIGN PATENT DOCUMENTS

CN        104955732 A    9/2015
CN        207191592 U    4/2018
(Continued)

OTHER PUBLICATIONS

International Search Report for PCT/EP2020/075081, dated Nov. 5, 2020, 5 pages.
(Continued)

*Primary Examiner* — Tuyen K Vo
(74) *Attorney, Agent, or Firm* — NIXON & VANDERHYE (57) ABSTRACT

Disclosed is a device for storing elements each including a first wireless communication unit, the device including: —a receiving support receiving the elements; —a second wireless communication unit generating waves and communicating with each first unit according to a communication protocol, a communication zone being a three-dimensional zone in which the second unit communicates with each first unit when each first unit is located in the zone and does not communicate with a first unit when the first unit is located outside the zone; —a waveguide able to guide the generated waves so that a dimension of the communication zone is strictly greater than a reference dimension, the reference
(Continued)

dimension being equal to the dimension of the communication zone when the storage device is without waveguides.

20 Claims, 7 Drawing Sheets (51) Int. Cl.
*H01Q 7/00* (2006.01)
*H04B 5/00* (2006.01)

(58) Field of Classification Search
CPC ..... G07F 9/026; G07F 17/0092; G07G 1/009; G16H 20/13; A61J 1/10; A61J 2205/60; H04W 4/80
See application file for complete search history.

(56) References Cited

U.S. PATENT DOCUMENTS

| | | | | |
|---|---|---|---|---|
| 11,706,907 B2* | 7/2023 | Elizondo, II | ........... | A61B 50/18 235/451 |
| 2007/0046552 A1* | 3/2007 | Marino | ................ | H01Q 1/44 340/572.1 |
| 2007/0257857 A1 | 11/2007 | Marino et al. | | |
| 2008/0316045 A1 | 12/2008 | Sriharto et al. | | |
| 2012/0137706 A1 | 6/2012 | Hussain et al. | | |
| 2015/0372369 A1* | 12/2015 | Tatomir | ................ | H01P 5/20 333/122 |
| 2017/0262797 A1* | 9/2017 | Wicks | ................ | G16H 40/40 |
| 2017/0286903 A1 | 10/2017 | Elizondo, II | | |
| 2018/0039803 A1 | 2/2018 | Elizondo, II | | |
| 2018/0254563 A1* | 9/2018 | Sonozaki | ............... | H01Q 13/18 |
| 2018/0372398 A1* | 12/2018 | Cosgrove | ............. | G06Q 20/208 |
| 2019/0220638 A1* | 7/2019 | Mongrenier | ....... | G06K 19/0723 |
| 2019/0305437 A1* | 10/2019 | Hamminga | ............ | H01Q 13/22 |
| 2020/0334426 A1* | 10/2020 | Pong | ................. | G06K 7/10415 |
| 2022/0083750 A1* | 3/2022 | Hussain | ............. | G06K 7/10168 |

FOREIGN PATENT DOCUMENTS

| | | |
|---|---|---|
| CN | 110199328 A | 9/2019 |
| EP | 1 647 919 A1 | 4/2006 |

OTHER PUBLICATIONS

Written Opinion of the ISA for PCT/EP2020/075081, dated Nov. 5, 2020, 10 pages.
Search Report for FR1909975, dated May 15, 2020, 2 pages.

* cited by examiner

DEVICE FOR STORING ELEMENTS, ASSOCIATED INSTALLATION AND ASSOCIATED COMMUNICATION METHOD

This application is the U.S. national phase of International Application No. PCT/EP2020/075081 filed Sep. 8, 2020 which designated the U.S. and claims priority to FR 19 09975 filed Sep. 10, 2019, the entire contents of each of which are hereby incorporated by reference.

BACKGROUND OF THE INVENTION

Field of the Invention

The present invention relates to a storage device for storing elements. The invention also relates to an installation for storing elements comprising such a storage device. The invention also relates to a communication method.

Description of Related Art

In the field of elements logistics, many specific systems have been developed due to the specificity of the elements or their content regarding transport or storage conditions.

This is in particular the case when the elements are bags containing biological products such as blood products (bags of primary blood, plasma, platelets, red blood cells, etc.) or cellular engineering products (stem cells, etc.), or drug bags such as chemotherapy bags.

It is known to store such bags in refrigerating structures comprising shelves for receiving bags. The bags stored in such structures generally comprise an identification tag, such as an RFID (radio frequency identification) tag, affixed on a face of the bag. Each tag stores information relative to the corresponding bag. Furthermore, such structures comprise a reader, such as an RFID reader, in order to read and update the information contained in the tags for said bags.

However, when the bags are arranged vertically on the shelves, the distance between the reader and the tags increases.

Furthermore, in this case, the RFID tags and the antenna of the RFID reader are arranged perpendicularly relative to one another.

As a result, the RFID reader cannot read all of the RFID tags.

There is therefore a need for a compact storage device able to read each tag reliably.

BRIEF SUMMARY OF THE INVENTION

To that end, the present description relates to a device for storing elements, each element comprising a first wireless communication unit, the storage device comprising a receiving support for receiving the elements, a second wireless communication unit able to generate waves, the second wireless communication unit being able to communicate with each first wireless communication unit according to a communication protocol, the communication zone also being defined as being a three-dimensional zone in which the second wireless communication unit is able to communicate with each first wireless communication unit when each first wireless communication unit is located in the communication zone, the second wireless communication unit not being able to communicate with at least one first wireless communication unit when the first wireless communication unit is located outside the communication zone, a waveguide able to guide the waves generated by the second wireless communication unit so that a dimension of the communication zone measured from the second wireless communication unit along a predetermined direction is strictly greater than a reference dimension, the reference dimension being equal to the dimension of the communication zone measured from the second wireless communication unit along the predetermined direction when the storage device is without waveguides.

According to specific embodiments, the device comprises one or more of the following features, considered alone or according to any technically possible combinations:
- the waves generated by the second wireless communication unit are electromagnetic waves including a magnetic field, the waveguide being a magnetic field concentrator suitable for concentrating the magnetic field generated by the second wireless communication unit.
- the waveguide is able to guide the waves generated by the second wireless communication unit in the predetermined direction.
- the size of the communication zone verifies one of the following properties: the size of the communication zone is greater than or equal to 105% of the reference value, the size of the communication zone is greater than or equal to 120% of the reference zone, and the size of the communication zone is less than or equal to 130% of the reference value.
- the waveguide comprises guide elements configured to guide the waves generated by the second wireless communication unit in the predetermined direction.
- the guide elements comprise two plates of equal sizes, parallel to one another, the two plates delimiting a guide channel between them for guiding the waves generated by the second wireless communication unit in the predetermined direction.
- the waveguide is made from metal, the metal in particular being aluminum.
- the reference value is equal to 86 millimeters and the first wireless communication unit is preferably a radiofrequency identification tag reader and comprises at least one antenna, which is preferably planar and in the shape of an eight, the radiofrequency identification tag reader optionally comprising a plurality of antennas having overlapping zones relative to one another.
- the elements of the plurality of elements are containers of biological products, medications or therapeutic preparations and each first wireless communication unit is a radiofrequency identification tag comprising a memory that is able to store a datum relative to the container bearing this first wireless communication unit.

The present description also relates to an element storage installation comprising an enclosure comprising an inner compartment, the enclosure preferably being a refrigerating enclosure, and comprising a storage device as previously described comprising a plurality of elements each bearing a first wireless communication unit, the second wireless communication unit being intended to communicate with each first wireless communication unit according to a communication protocol, the storage device being arranged in the inner compartment.

The present disclosure further relates to a communication method between at least a first wireless communication unit and a second wireless communication unit implemented in a device for storing elements, each element comprising a first wireless communication unit, the device for storing elements comprising a receiving support intended to receive the elements, a second wireless communication unit able to generate waves, the second wireless communication unit being able to communicate with each first wireless communication unit using a communication protocol, a communication zone also being defined as being a three-dimensional zone in which the second wireless communication unit is able to communicate with each first wireless communication unit when each first wireless communication unit is located in the communication zone, the second wireless communication unit not being able to communicate with at least one first wireless communication unit when the first wireless communication unit is located outside the communication zone, a waveguide able to guide the waves generated by the second wireless communication unit so that a dimension of the communication zone measured from the second wireless communication unit along a predetermined direction is strictly greater than a reference dimension, the reference dimension being equal to the dimension of the communication zone measured from the second wireless communication unit along the predetermined direction when the storage device is without waveguide, the method comprising a step for transmitting waves by means of the second wireless communication unit, during the step for transmitting, the dimension of the communication zone measured from the second wireless communication unit along the predetermined direction is greater than or equal to the reference dimension.

According to one particular embodiment of the method, the waveguide comprises guide elements configured to guide the waves generated by the second wireless communication unit in the predetermined direction, the guide elements comprising two plates of equal sizes, parallel to one another delimiting a channel between them, during the step for transmitting waves by the second wireless communication unit, the second wireless communication unit transmits electromagnetic waves comprising a magnetic field and the two plates concentrate, in the channel, the magnetic field emitted by the second wireless communication unit.

The present description also relates to a wireless communication device comprising at least three elementary antennas each comprising at least two loops, two adjacent loops being configured to be traveled through by currents having opposite circulation directions, each loop of each antenna delimiting an inner surface called loop surface, in which the elementary antennas are offset two by two in a rectilinear direction and in which, for each loop of each antenna, a part of the surface of this loop is superimposed with a portion of a loop surface of each other elementary antenna, the part of said loop surface having an area smaller than the area of the loop surface of said loop.

According to specific embodiments, the wireless communication device comprises one or more of the following features, considered alone or according to any technically possible combinations:
  a part of each loop of each antenna, called coinciding part, coincides with a loop portion of each other antenna and, for each loop, the coinciding part is at least greater than 5% of the perimeter of this loop.
  the loops of each antenna have the same shape.
  each antenna is planar and the at least three elementary antennas extend in a same plane.
  each elementary antenna comprises at least three loops.
  each loop of each antenna is partitioned into loop partitions having a surface, each loop partition being delimited by at least one loop part of a loop of another antenna, each surface of a loop partition having an area of less than or equal to one third of the area of the surface of this loop, and the elementary antennas extend in a same plane and are configured to emit an electromagnetic field in a three-dimensional spatial zone, the electromagnetic field emitted in the three-dimensional zone being continuous along a direction parallel to the rectilinear direction.
  the wireless communication device is a radio frequency identification tag reader.

The present description further relates to an element storage installation, each element bearing a first wireless communication unit, the installation comprising an enclosure comprising an inner compartment, the enclosure preferably being a refrigerating enclosure, and comprising a wireless communication device as previously described, forming a second wireless communication unit able to communicate with at least a first wireless communication unit in which the wireless communication device is arranged in the inner compartment.

According to one particular embodiment of the element storage installation, the elements are containers of biological products, medications or therapeutic preparations, and each second wireless communication unit is a radiofrequency identification tag comprising a memory able to store a datum relative to the container bearing this second wireless communication unit.

The present description also relates to a communication method carried out in an element storage installation as previously described between at least a first wireless communication unit and a second wireless communication unit, the second wireless communication unit comprising at least three elementary antennas each comprising at least two loops, two adjacent loops being configured to be traveled through by currents having opposite circulation directions, each loop of each antenna delimiting an inner surface called loop surface, in which the elementary antennas are offset two by two along a rectilinear direction, and in which, for each loop of each antenna, the part of the surface of this loop is superimposed with a portion of a loop surface of each other elementary antenna, the part of said loop surface having an area smaller than the area of the loop surface of said loop, wherein the communication method comprises a step for wave transmission by the wireless communication device.

BRIEF DESCRIPTION OF THE SEVERAL VIEWS OF THE DRAWINGS

Other features and advantages of the invention will appear upon reading the following description of one embodiment of the invention, provided as an example only and in reference to the drawings, which are.

DETAILED DESCRIPTION OF THE INVENTION

Figure 1:
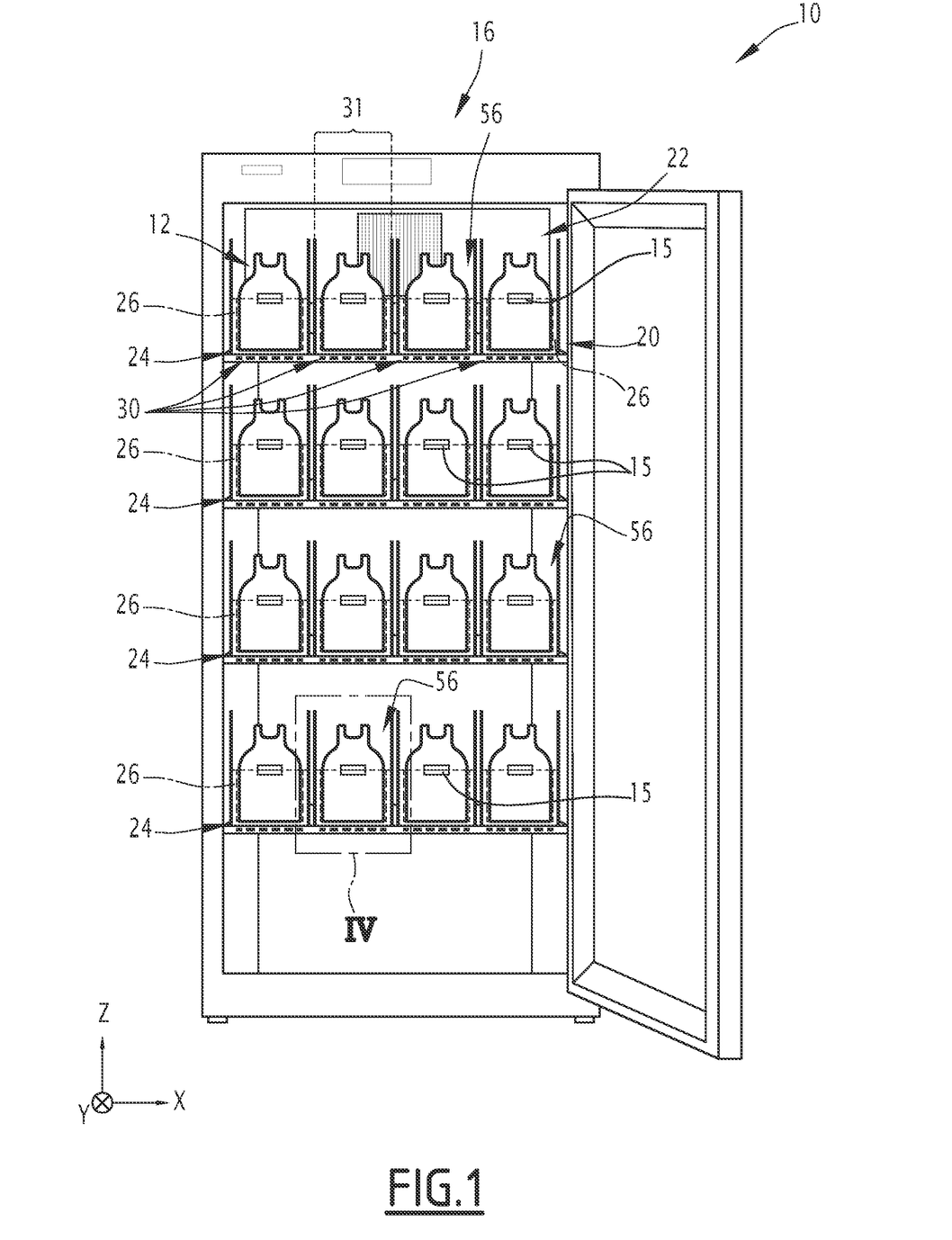
FIG. 1, a schematic perspective illustration of an installation comprising a device for storing elements, FIG. 2, a schematic illustration of an element, FIG. 3, a view of a part of the device for storing elements of FIG. 1, FIG. 4, an enlarged sectional schematic view of part of FIG. 3, identified by arrow IV in FIG. 1, including a receiving tray, FIG. 5, a view of FIG. 4 further showing communication zones, FIG. 6, a schematic illustration of a second wireless communication unit, and FIG. 7, an exploded schematic illustration of part of the second wireless communication unit of FIG. 6.

FIG. 1 shows an installation 10 for storing elements 12.

The installation 10 is for example used to keep each element 12 at a predefined temperature and/or to shake each element 12.

A transverse direction is also defined in the present description. The transverse direction is shown by the axis X and referred to in the remainder of the description as the "transverse direction X".

A longitudinal direction perpendicular to the transverse direction X is also defined. The longitudinal direction is shown by an axis Y and referred to in the remainder of the description as the "longitudinal direction Y".

A vertical direction perpendicular to the transverse direction X and the longitudinal direction Y is also defined. The longitudinal direction is shown by an axis Y and referred to in the remainder of the description as the "vertical direction Z".

Furthermore, the size of an object of the installation 10 along the transverse direction X is referred to hereinafter as the "width". The size of an object of the installation 10 along the longitudinal direction Y is called "length". The size of an object of the installation 10 along the vertical direction Z is called "height".

Furthermore, in the present description, a value V that is inclusively between a first value V1 and a second value V2 means that the value V is greater than or equal to the first value V1 and that the value V is less than or equal to the value V2.

Figure 2:
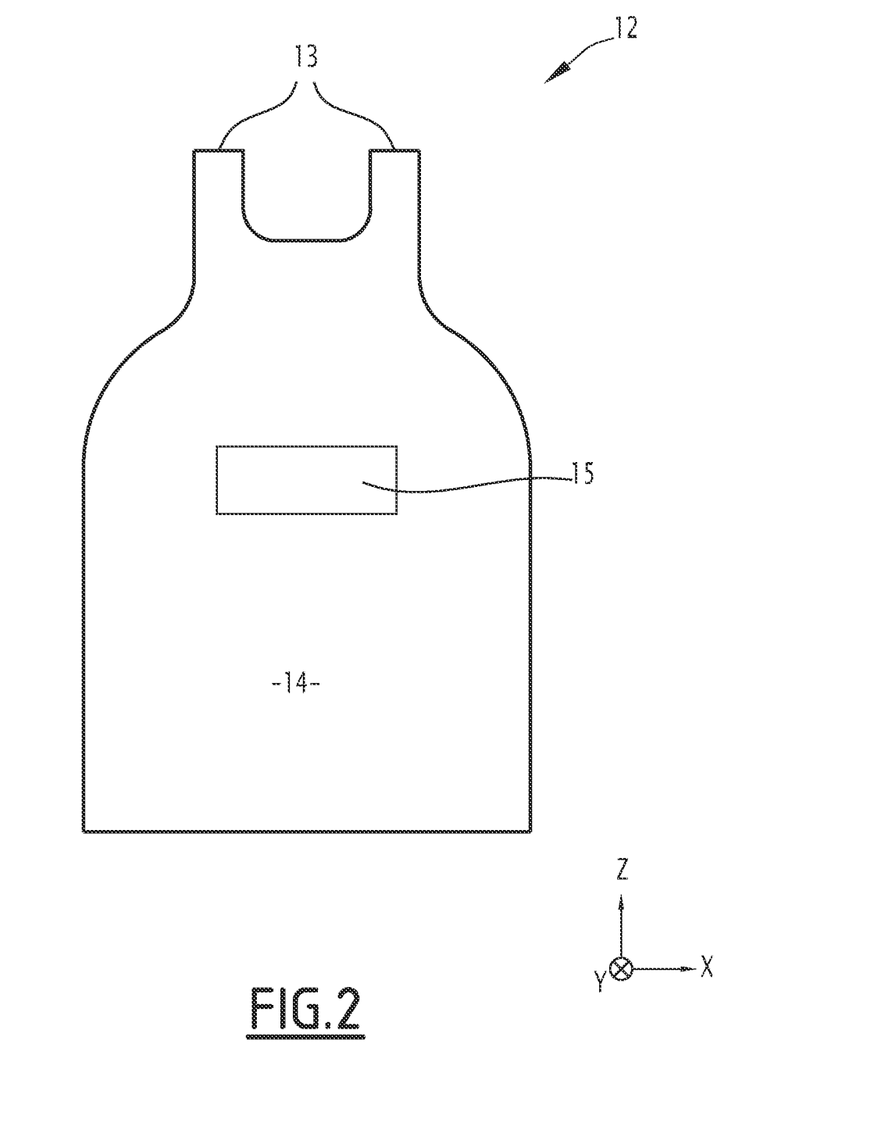

In reference to FIG. 2, according to the described example, the elements 12 are containers. Generally, a container refers to any type of bag that is intended to contain products whose use is subject to strict storage constraints.

More particularly, the elements 12 are for example bags containing biological products such as blood products (bags of primary blood, plasma, platelets, red blood cells, etc.) or cellular engineering products (human or animal cells, in particular human or animal stem cells, products from human or animal cells).

In a variant, the elements 12 are drug bags or therapeutic preparation bags containing one or more active ingredients or medications, such as chemotherapy bags (generally containing a solute and one or more chemotherapy active ingredients).

More generally, the elements 12 can contain any product designed to be infused in a human or animal.

According to the considered example, each container 12 is a bag intended to contain plasma in the case at hand.

In a known manner, such a container 12 is a plasma-tight container made from a breathable plastic material allowing metabolism, of the PVC (polyvinyl chloride), polycarbonate or PEG (polyethylene glycol) type.

The container 12 includes tubings 13 that are closed off, for example by welding.

These tubings 13 were used, before being closed off, to insert the plasma into the container 12.

The container 12 further has two large faces 14 (only one is visible in FIG. 2).

In FIG. 2, the container 12 is arranged vertically, that is to say its two large faces 14 are substantially perpendicular to the plane defined by the transverse direction X and the longitudinal direction Y.

Each element 12 comprises a first wireless communication unit 15.

Each first communication unit 15 is for example a tag, such as an adhesive tag fastened on an outer wall of the element. In particular, the adhesive tag is fastened on one of the large faces 14 of the container 12.

In general, each first communication unit 15 comprises at least an antenna, a memory, and optionally a microprocessor.

The antenna of each first communication unit 15 is for example a radiofrequency antenna, and is known as a radiofrequency identification tag, or RFID tag.

The memory of each first communication unit 15 comprises information relative to the corresponding element 12.

Such information is for example: a unique identifier of the element 12, the storage date of the element 12, the expiration date of the element 12, the date on which the first communication unit 15 of the element 12 communicated information for the first time, the donation number related to the contents of the element 12, the product code for the contents of the element 12, the rhesus group of the contents of the element 12, the blood phenotype of the product of the element 12, the identity of the patient from whom the contents of the element 12 originated, the name of the patient from whom the contents of the element 12 originated, the product of the contents of the element 12, the donation center (including the address) where the contents of the element 12 were obtained, the process in progress for the element 12 and the anticoagulant type of the contents of the element 12. In the case of chemotherapy, such information further comprises the production date, the product type, the identity of the prescribing doctor, the identity of the pharmacist, the identity of the manufacturer, the release date and the status (released, delivered, etc.).

The installation 10 comprises an enclosure 16 and a device 20 for storing elements 12.

The enclosure 16 delimits an inner compartment 22 for receiving the storage device 20.

The enclosure 16 is for example a refrigerating enclosure, such as a refrigerator or a freezer. When the refrigerating enclosure is a refrigerator, the temperature of the enclosure is inclusively between 0° C. and 5° C., preferably equal to 4° C. When the refrigerating enclosure is a freezer, the temperature of the enclosure is inclusively between −35° C. and −96° C., preferably equal to −40° C.

In a variant, the enclosure 16 is a platelet agitator. The enclosure 16 is then for example integrated into an incubator having a temperature preferably equal to 24° C.

In the present description, relative positions are defined with respect to a current usage direction of the enclosure 16. In particular, a bottom is defined corresponding to the floor, and a top opposite the bottom. Thus, in the remainder of the application, a first element said to be "lower" than a second element is located closer to the floor than the second element. Furthermore, a first element said to be "higher" than a second element is located further from the floor than the second element. This relative positioning is also shown by terms such as "below" or "above", "lower" or "upper".

The storage device 20 comprises at least one receiving support 24, 26, at least one second wireless communication unit 30, at least one waveguide 31 and at least one communication zone 32.

In the case at hand, the storage device 20 comprises a plurality of receiving supports 24, 26.

Each receiving support 24, 26 comprises a shelf 24 and at least one receiving tray 26.

Figure 3:
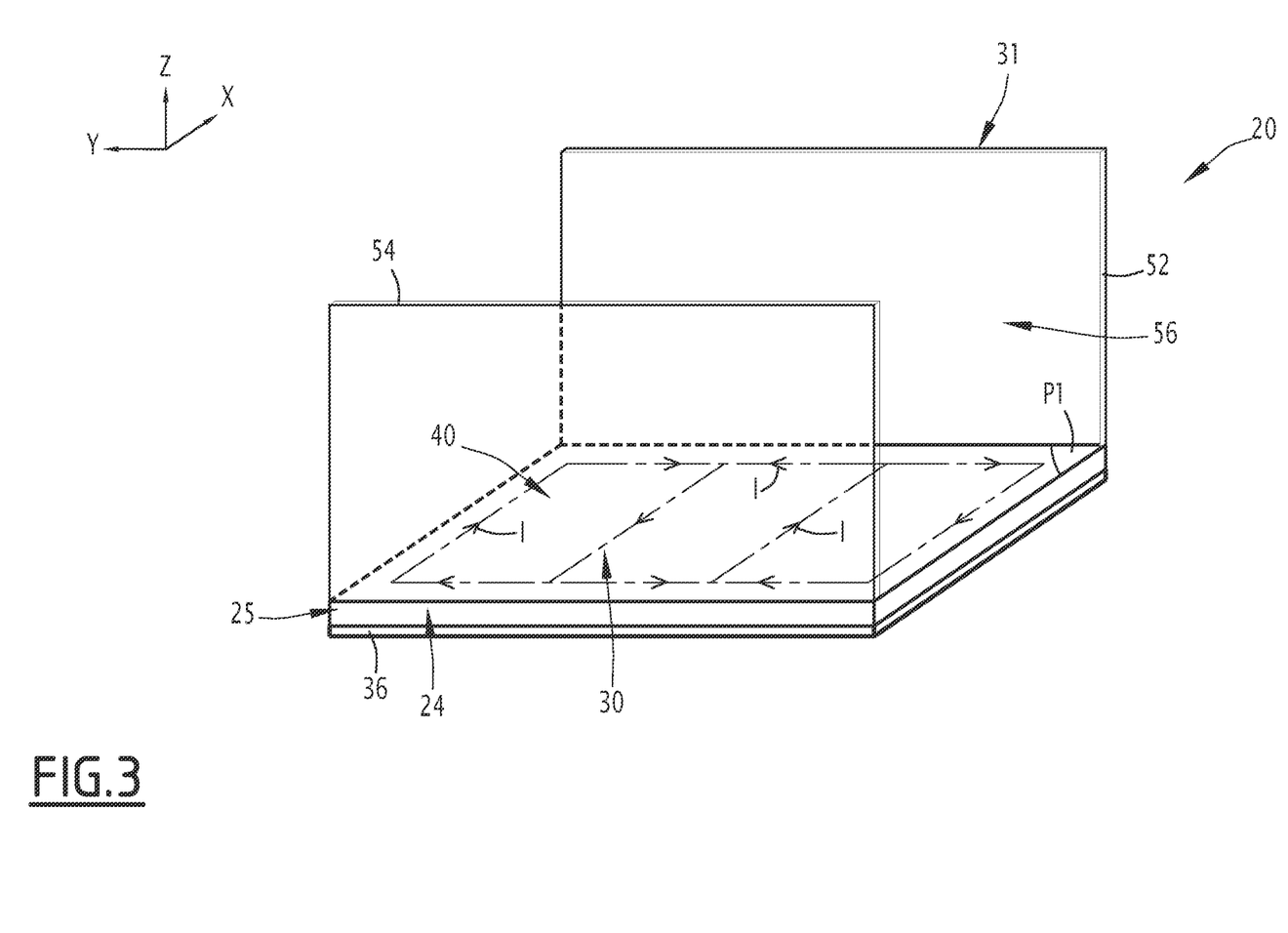
Figure 4:
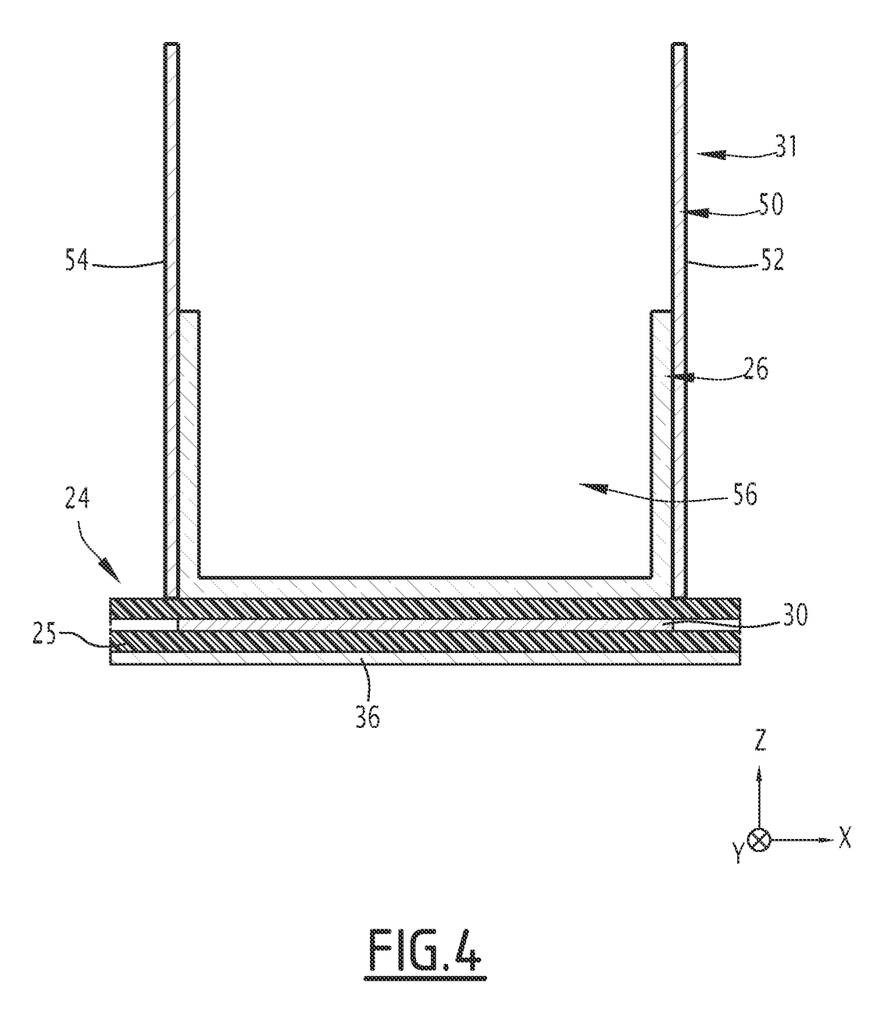

The receiving supports 24, 26 are described in detail in reference to FIGS. 3 and 4 showing a part of a single shelf 24.

Each shelf 24 comprises a body 25.

The body 25 of the shelf 24 is for example made from plastic.

The lower face of the body 25 comprises a layer 36 of a material preventing the passage of electromagnetic waves through the shelf 24. Such a layer 36 of material is also known as "electromagnetic shielding".

As an illustration, each receiving support 24, 26 comprises a plurality of receiving trays 26.

The upper face of each shelf 24 is able to receive the plurality of receiving trays 26.

For example, the upper face of each shelf 24 is able to receive at least four receiving trays 26.

For example, the receiving trays 26 of a given shelf 24 are juxtaposed in the inner compartment 22 along the transverse direction X. Furthermore, for example, each receiving tray 26 extends over the entire width of the shelf 24.

Each receiving tray 26 is made from a material transparent to electromagnetic waves. For example, the material is a plastic.

Each receiving tray 26 is able to receive a plurality of elements 12 arranged vertically.

In each receiving tray 26, the plurality of elements 12 is arranged in the form of a row of elements 12 along the longitudinal direction Y.

As an example, in each receiving tray 26, the distance between two elements 12 measured in the longitudinal direction Y is for example equal to 15 millimeters (mm).

In the present exemplary embodiment, the storage device 20 comprises a plurality of second wireless communication units 30. Each second wireless communication unit 30 is also called "wireless communication device" in the present application.

A plurality of second communication units 30 is for example arranged in a separate shelf 24. The second communication units 30 are shown in dotted lines in FIG. 1.

Each second communication unit 30 is arranged opposite a row of first communication units 15 of a given receiving tray 26 in the vertical direction Z. Furthermore, each second communication unit 30 is arranged below the row of first communication units 15.

For each shelf 24, the plurality of second communication units 30 is arranged in the upper part of the shelf 24. In particular, each second communication unit 30 is located just below the upper surface of each shelf 24. Each shelf 24 then forms a satellite containing the plurality of second units 30. The satellite is a case that contains the plurality of second units 30.

Each second communication unit 30 of a shelf 24 is able to communicate with the first communication units 15 of the elements 12 borne by a given receiving tray 26 of this shelf 24.

In the remainder of the description, the first communication units 15 supported by a shelf 24 and intended to communicate with the second communication unit 30 of this shelf are called "first communication units 15 associated with the second communication unit 30".

Each second communication unit 30 is able to communicate with each first communication unit 15 associated with this second communication unit 30 according to a communication protocol.

For example, the communication protocol is an RFID protocol.

For example, the RFID communication protocol is a communication protocol called "UHF" protocol. The acronym "UHF" stands for ultrahigh frequency.

In such a communication protocol, each second communication unit 30 is able to transmit or receive a signal having a frequency inclusively between 300 MHz and 3000 MHz.

For example, the RFID communication protocol is a communication protocol called "HF" protocol. The acronym "HF" stands for high frequency.

In such a communication protocol, each second communication unit 30 is able to transmit or receive a signal having a frequency inclusively between 3 MHz and 30 MHz.

According to one particular example, the frequency is equal to 13.56 MHz±7 kHz.

According to one exemplary embodiment, each second communication unit 30 is able to operate both according to the UHF RFID communication protocol and the HF RFID communication protocol.

In particular, each second communication unit 30 is an RFID reader. In other words, each second communication unit 30 is able to read the information stored in each first communication unit 15 associated with this second communication unit 30.

Each second communication unit 30 comprises at least one elementary antenna 40.

The elementary antenna 40 is for example an RFID antenna. In other words, the elementary antenna 40 is able to emit radiofrequency waves.

Several communication zones 32 are also defined.

Each communication zone 32 is associated with a separate second communication unit 30.

Each communication zone 32 associated with a second communication unit 30 is a three-dimensional zone in which this second communication unit 30 is able to communicate with each associated first communication unit 15 when each first communication unit 30 is located in the communication zone 32, the second communication unit 30 not being able to communicate with at least one first communication unit 15 when this first communication unit 15 is outside the communication zone 32.

The storage device 20 comprises a plurality of waveguides 31.

Each waveguide 31 is associated with a given second communication unit 30. Thus, in the present exemplary embodiment, each waveguide 31 is associated with a given receiving tray 26.

Hereinafter, a single waveguide 31 is described. Each other waveguide 31 is similar to the waveguide 31 described hereinafter.

The waveguide 31 is able to guide the waves generated by each second communication unit 30 so that a dimension H of each communication zone 32 measured from this associated second communication unit 30 along a predetermined direction is strictly greater than a reference dimension HR.

For each communication zone 32, the reference dimension HR is equal to the dimension of this communication zone 32 measured from the associated second communication unit 30 along the predetermined direction when the storage device 20 is without waveguides 31.

Each communication zone 32 will be described later during the description of the communication method.

The waveguide 31 is visible in FIGS. 3 and 4.

In the present example, the waveguide 31 is able to guide the waves generated by each second communication unit 30 along the vertical direction Z forming the predetermined direction.

The waveguide 31 comprises guide elements 50 configured to guide the waves emitted by each second communication unit 30 in the vertical direction Z.

For example, the guide elements 50 comprise a first plate 52 and a second plate 54. The first plate 52 and the second plate 54 are parallel and normal to the transverse direction X.

In this example, the two plates 52, 54 are arranged on either side of the receiving tray 26 and spaced apart from one another in the transverse direction X. For example, each plate 52, 54 is arranged against a respective wall of the receiving tray 26.

Advantageously, the first plate 52 and the second plate 54 of the waveguide 31 are separated.

For example, each plate 52, 54 is fastened to a respective wall of the tray 26. As an illustration, each plate 52, 54 is fastened by gluing.

As an illustration, the two plates 52, 54 have equal dimensions.

The two plates 52, 54 delimit a guide channel 56 between them for guiding waves generated by each second communication unit 30 in the predetermined direction, that is to say the vertical direction Z.

For example, the guide channel 56 has a length at least equal to the length of the second communication units 30.

The waveguide 31 is made from metal. The metal is for example aluminum. Thus, each plate 52, 54 is made from aluminum.

Owing to the waveguide 31, the height H of the communication zone 32 for the storage device 20 comprising the waveguide 31 is strictly greater than the reference height HR of the communication zone 32 of a storage device 20 not comprising a waveguide 31.

Thus, the performance of the device 20 for storing elements 12 is improved relative to the storage devices of the state of the art.

Indeed, the storage device 20 makes it possible to position the elements 12 vertically and perpendicular to the second communication units 30, and to read all of the first communication units 15 borne by these elements 12.

Furthermore, the storage device 20 makes it possible to store more elements 12 while ensuring reliable reading of each first communication unit 15.

The present description therefore relates to the element 12 storage installation 10 comprising a device 20 for storing elements as previously described.

Figure 6:
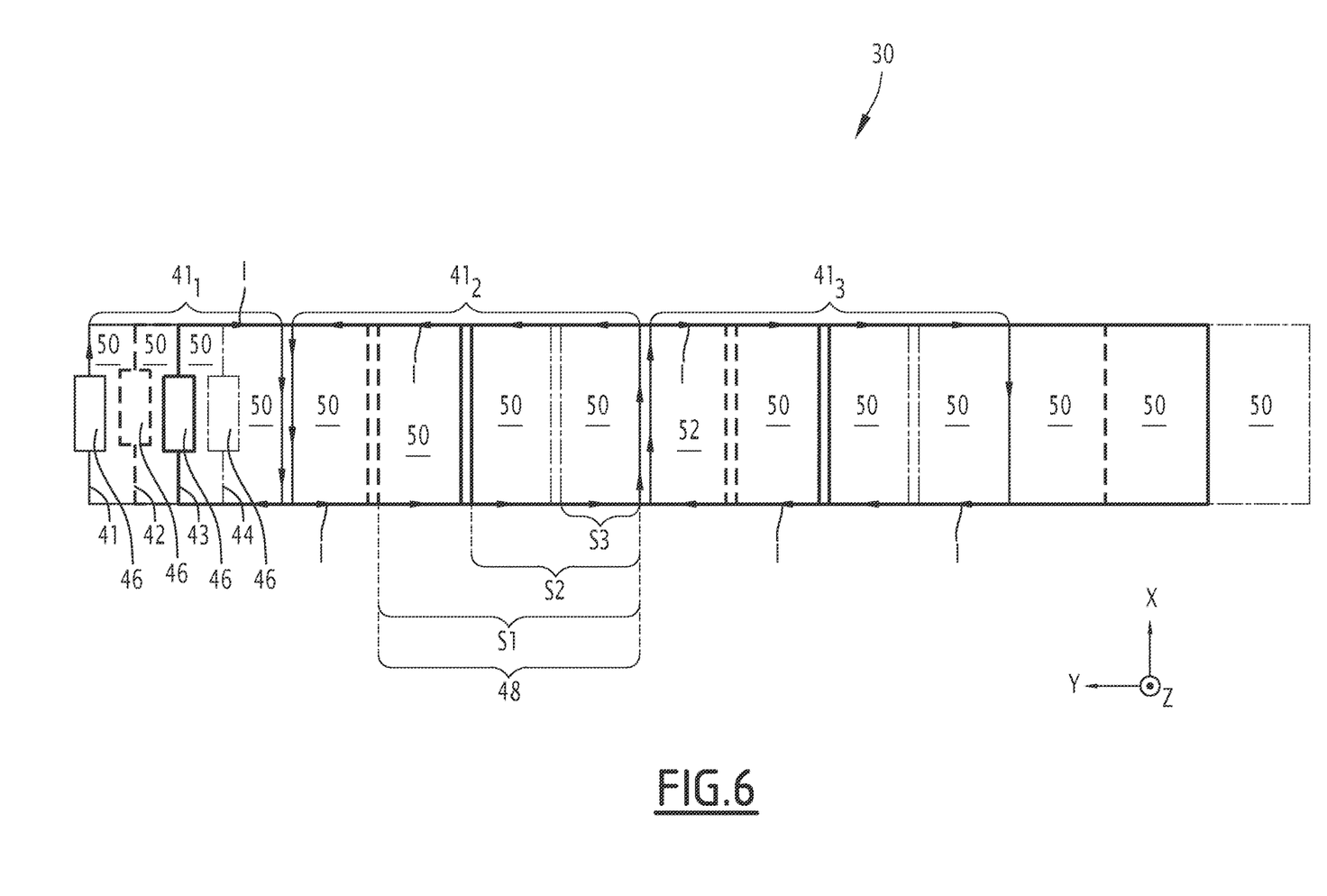
Figure 7:
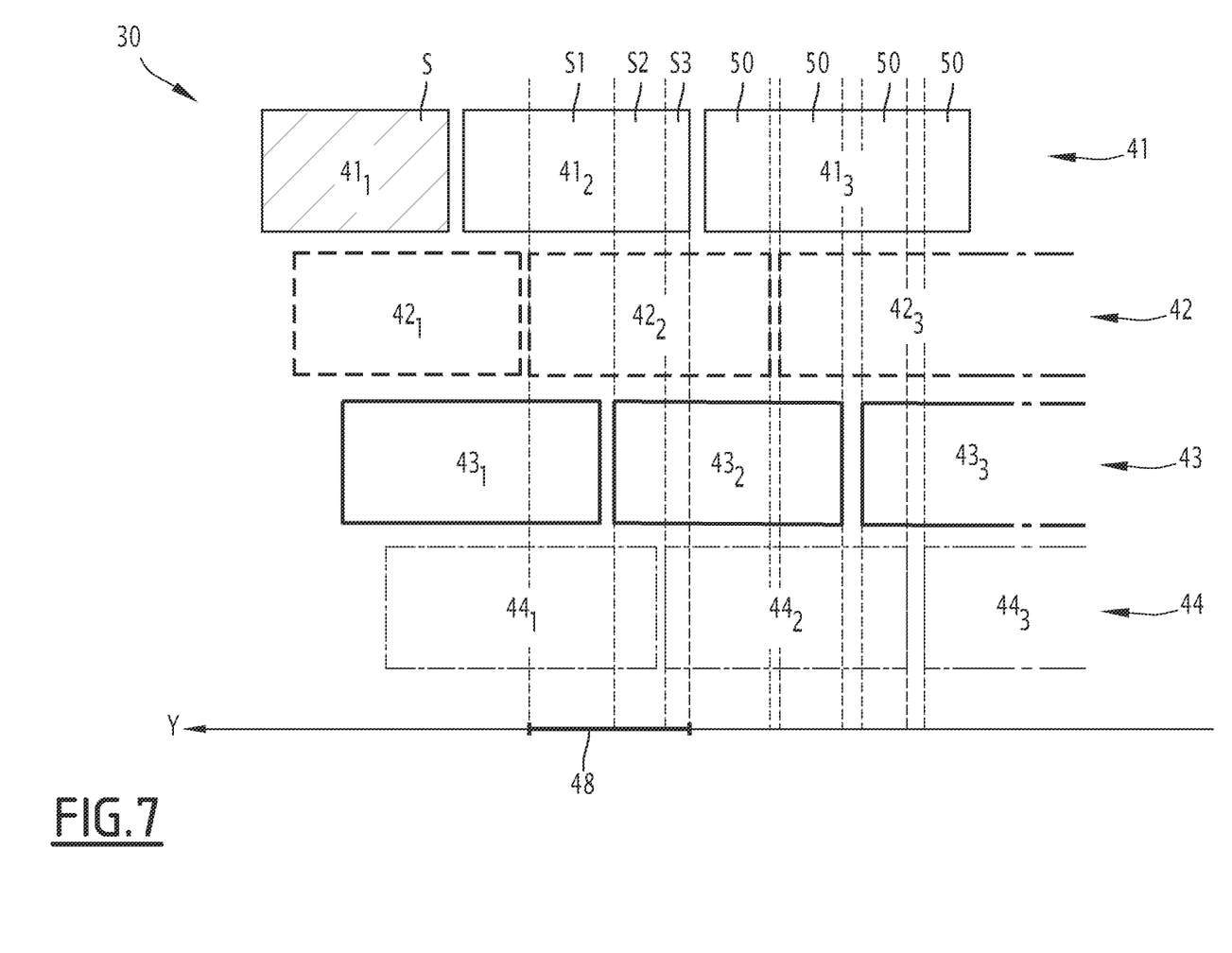

In reference to FIGS. 6 and 7, the present description further relates to a particular example of a second communication unit 30 that may be part of the installation 10 and/or the storage device 20.

In one specific embodiment of the storage device 20, each second communication unit 30 previously described is similar to the second communication unit 30 described hereinafter.

The second communication unit 30 comprises four elementary antennas 40.

In the remainder of the present description, the four elementary antennas are called "first antenna 41", "second antenna 42", "third antenna 43", "fourth antenna 44" when a specific elementary antenna among the four elementary antennas 40 is designated. In the case where no specific elementary antenna 40 is designated, the generic term "antenna 40" is used.

For example, each antenna 40 is an RFID antenna. Thus, each antenna 40 is able to emit electromagnetic waves, and more specifically radiofrequency waves.

The emitted frequency of the radiofrequency waves is inclusively between 13.56 MHz±7 kHz.

Each 40 antenna is a communication antenna. Thus, the antennas 40 are adapted to communicate with the first communication units 15.

For example, each antenna 40 is a figure-eight antenna.

In the case at hand, each figure-eight antenna 40 comprises N1 loops.

The number N1 of loops is greater than or equal to 2. For example, the number N1 of loops is equal to three.

Each 40 antenna is unitary. Thus, each antenna 40 is in the form of a single piece, meaning that each antenna 40 does not have separate parts.

In the remainder of the description, each loop of each antenna 40 is identified by an index i, i being a whole number and varying from 1 to N1.

Furthermore, each antenna 40 of each second communication antenna 30 comprising several loops $41_i$ to $44_i$ is also called "coiled antenna". In the present exemplary embodiment, the loops $41_i$ to $44_i$ are aligned relative to one another along the longitudinal direction Y.

Each loop $41_i$ to $44_i$ is delimited by an electrically conductive wire able to be traveled by a current I.

For example, each loop 41i to 44i has a closed contour.

Each antenna 40 further comprises a supply connector 46 supplying current to the considered connector 40.

For example, the supply connectors 46 of the antennas 40 are parallel to one another in the longitudinal direction Y.

For example, each loop $41_i$ to $44_i$ of each antenna 40 has a rectangular shape.

Thus, each loop $41_i$ to $44_i$ has a first and a second pair of parallel opposite sides. In the case at hand, the first pair of opposite sides is parallel to the transverse direction X and the second pair of opposite sides is parallel to the longitudinal direction Y.

In each figure-eight antenna 40, two adjacent loops $41_i$ to $44_i$ are configured to be traveled through by currents I having opposite circulation directions. The circulation direction of the current I is shown only for the first antenna 41. The circulation direction of the current I shown only for the first antenna 41 is transposable for the other antennas 42 to 44.

The antennas 40 are planar, that is to say the antennas 40 extend in a same plane P1. As an example, the plane P1 is defined by the transverse direction X and the longitudinal direction Y.

For example, the length of each loop $41_i$ to $44_i$ corresponds to the dimension of each side of the second pair of sides opposite this loop $41_i$ to $44_i$. For example, the length is inclusively between 45 mm and 180 mm.

For example, the width of each loop $41_i$ to $44_i$ corresponds to the dimension of each side of the first pair of sides opposite this loop $41_i$ to $44_i$. For example, the width is inclusively between 87 mm and 111 mm.

As shown in FIG. 7, which is an exploded view of part of FIG. 6, each loop $41_i$ to $44_i$ of each antenna 40 delimits an inner surface S called "loop surface". The surface S of the first loop $41_1$ of the first antenna 41 is crosshatched in this FIG. 7.

Furthermore, the first antenna 41, the second antenna 42, the third antenna 43 and the fourth antenna 44 are offset two by two successively in a rectilinear direction. In the case at hand, the rectilinear direction is the alignment direction of the loops $41_i$ to $44_i$, that is to say the longitudinal direction Y.

In other words, the position of the antennas 40 is obtained by the translation of the antennas 40 relative to one another along the longitudinal direction Y. The translation of the antennas 40 relative to one another is done in a same direction.

Thus, the position of the second antenna 42 is obtained by the translation of the first antenna 41 in the longitudinal direction Y, the position of the third antenna 43 is obtained by the translation of the second antenna 42 in the longitudinal direction Y and the position of the fourth antenna 44 is obtained by the translation of the third antenna 43 in the longitudinal direction Y.

In a variant, the rectilinear direction is the transverse direction X.

Also in a variant, the rectilinear direction is the vertical direction Z.

The antennas 40 are for example offset two by two by a dimension smaller than the smallest dimension of a loop $41_i$ to $44_i$ measured along the longitudinal direction Y.

In FIG. 7, the offset of the antennas 40 relative to one another along the longitudinal direction Y is visible.

For each loop $41_i$ to $44_i$ of each antenna 40, a part of the surface S of this loop $41_i$ to $44_i$ is superimposed with a portion of the loop surface of each other antenna 40. In other words, the loop surface parts are overlapping zones of the antennas 40 with one another.

The expression "for each loop $41_i$ to $44_i$ of each antenna 40, a part of the S surface of that 41i to 44i loop is superimposed with a portion of the loop surface of each other antenna 40" means that for each loop 41i to 44i of each antenna 40, a portion of the surface S of this loop $41_i$-$44_i$ is overlaid by a portion of a loop-surface of each other antenna 40.

Thus, for each loop $41_i$ to $44_i$ of each antenna 40, a part of the surface S of this loop $41_i$ to $44_i$ is covered by a portion of a loop surface of each other antenna 40 along a covering direction. The covering direction is, for example, perpendicular to the P1 plane in which the antennas 40 extend.

The aforementioned loop surface parts are described in detail hereinafter for the second loop $41_2$ of the first antenna 41 only and are similarly defined for all of the other loops $41_i$ to $44_i$ of each antenna 40.

Three loop surface parts are defined for the second loop $41_2$, called first loop surface S1, second loop surface S2 and third loop surface S3.

Each surface part S1, S2, S3 is a part of the surface S of the second loop $41_2$.

The first part S1 corresponds to the part of the surface of the second loop $41_2$ of the first antenna 41 covered by a portion of the second loop $42_2$ of the second antenna 42. As shown in FIG. 7, the first part S1 includes the second and third parts S2 and S3.

The second part S2 corresponds to the part of the second loop $41_2$ of the first antenna 41 covered by a portion of the second loop $43_2$ of the third antenna 43. As also shown in FIG. 7, the second part S2 includes the third part S3.

The third part S3 corresponds to the part of the second loop $41_2$ of the first antenna covered by a portion of the second loop $44_2$ of the fourth antenna 44.

The area of each loop surface part S1, S2, S3 is smaller than the area of the surface S of the second loop $41_2$.

As a result, the second loop $41_2$ of the first antenna 41 is superimposed with a surface portion of the loop $42_2$, $43_2$, $44_2$ of each other antenna 42 to 44.

Furthermore, several coinciding parts are defined for each loop $41_i$ to $44_i$ of each antenna 40.

For each loop $41_i$ to $44_i$ of each antenna 40, each coinciding part coincides with a loop portion of each other antenna 40. In other words, each coinciding part of each loop $41_i$ to $44_i$ is substantially superimposed with a loop portion of each other antenna 40.

As an illustration, a coinciding part of the second loop $41_2$ of the first antenna 41 with the second loop $42_2$ of the second antenna 42 is identified by reference sign 48.

In FIG. 7, for greater convenience, the coinciding part 48 is shown on the axis Y indicating the longitudinal direction Y.

For each loop $41_i$ to $44_i$, each coinciding part is at least greater than 5% of the perimeter of this loop $41_i$ to $44_i$.

In the case at hand, for each loop $41_i$ to $44_i$, the coinciding part of this loop $41_i$ to $44_i$ is parallel to the longitudinal direction Y.

Furthermore, the arrangement of the antennas 40 relative to one another is such that each loop $41_i$ to $44_i$ of each antenna 40 is partitioned into several loop partitions. Each loop partition is identified by reference sign 50.

The demarcations of each partition 50 for the third loop $41_3$ of the first antenna are visible in FIG. 7. The demarcations result from the projection of each loop of each other antenna 42, 43, 44 on the third loop $41_3$ of the first antenna 41.

Each loop partition 50 is delimited by at least one loop part of two separate antennas 40.

Each loop partition 50 has a loop partition surface strictly smaller than each surface S of each loop $41_i$ to $44_i$.

According to one particular exemplary embodiment, the length of each partition 50 is equal to 38 mm.

Preferably, the area of the surface of the partitions 50 is less than or equal to one third of the area of the surface of this loop $41_i$ to $44_i$. According to this same particular embodiment, the length of each partition 50 is less than or equal to one third of the length of this loop $41_i$ to $44_i$.

According to one particular embodiment, for each loop $41_i$ to $44_i$, the surface area of one or several partition(s) 50 is equal to 1/N2 of the surface area S of this loop $41_i$ to $44_i$, where N2 is equal to the number of antennas 40 of the second communication unit 30. According to this same particular embodiment, the length of one or several partition(s) 50 of each loop $41_i$ to $44_i$ is less than or equal to 1/N2 of the length of this loop $41_i$ to $44_i$.

The electromagnetic field emitted by each second communication unit 30 along a direction parallel to the longitudinal direction Y.

In other words, each second communication unit 30 is configured to emit an electromagnetic field that has no hole along the length of the second communication unit 32.

For example, the antennas 40 are integrated into a printed circuit board (not shown). Thus, since each second communication unit 32 comprises several superimposed antennas 40, there is no reading hole of the first communication units along the longitudinal direction Y.

Advantageously, the length of the antennas 40 is such that the orthogonal projection of each first communication unit 15 in the plane P1 is included in at least one loop $41_i$ to $44_i$ of one of the antennas 40.

Figure 5:
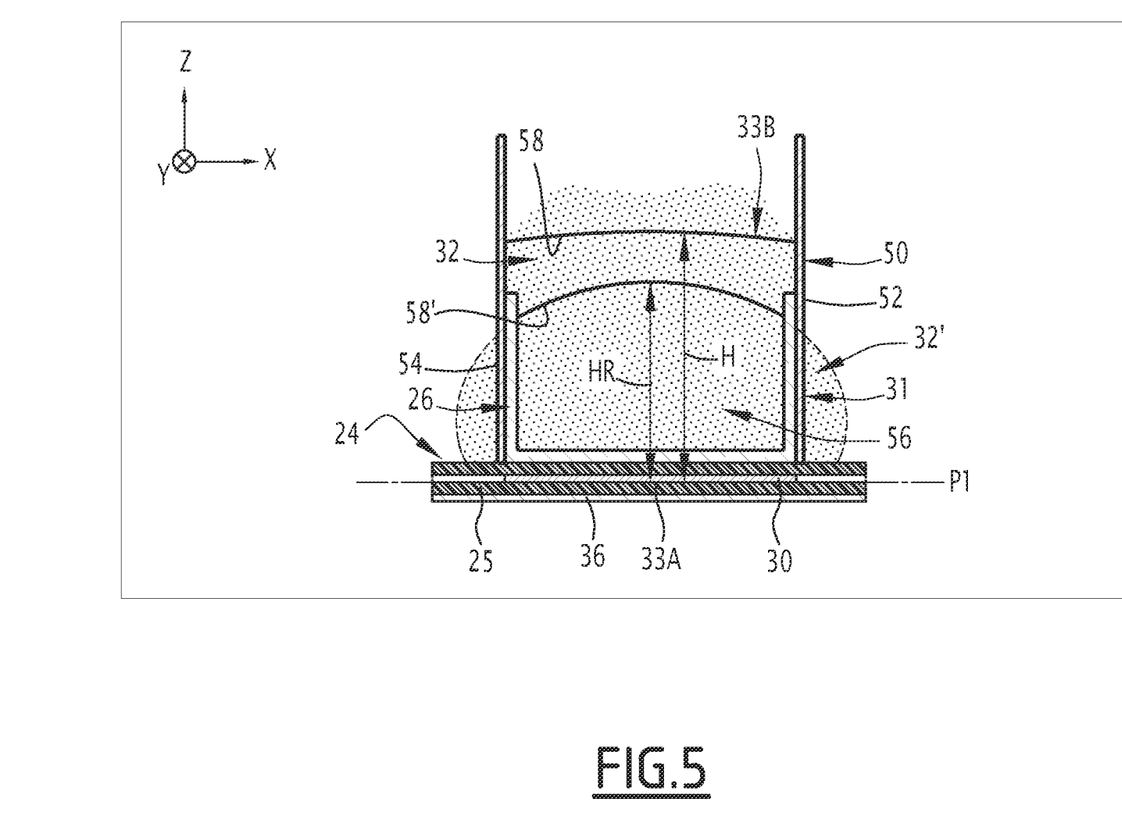

A communication method between a first communication unit 15 and a second communication unit 30 is described in the remainder of the present description in reference to FIG. 5.

The method comprises an initial step for supplying current I to the antennas 40 of the second communication unit 30.

For example, the value of the current I is inclusively between 20 milliamperes (mA) and 120 mA.

The method comprises a step for transmitting electromagnetic waves by means of the second communication unit 30.

The transmission power of the second communication unit 30 is for example equal to 1.2 Watts.

The transmission power is constant.

The electromagnetic field emitted by the second communication unit 30 is shown by small dots in FIG. 5.

The second communication unit 30 emits a continuous electromagnetic field along the longitudinal direction Y (that is to say without reading holes along the longitudinal direction Y).

The second communication unit 30 emits a continuous electromagnetic field along the transverse direction X (that is to say without reading holes along the transverse direction X).

Furthermore, the waveguide 31 guides the electromagnetic waves generated by the second communication unit 30 along the vertical direction Z.

More specifically, the electromagnetic waves are guided by the guide channel 56 toward the upper part of the inner compartment 22, that is to say along the vertical direction Z.

The three-dimensional zone of the inner compartment 22 receiving the electromagnetic waves emitted by the second communication unit 30 is called "reception zone".

The communication zone 32 is part of the reception zone.

The communication zone 32 extends from the second communication unit 30 along the vertical direction Z.

In a plane normal to the longitudinal direction Y, the communication zone 32 is delimited by a first end 33A and a second end 33B that are spaced apart from one another along the vertical direction Z.

The first end 33A is combined with the plane P1 in which the elementary antenna 40 of the second communication unit 30 extends.

The second end 33B depends on the power $\pi$ of the electromagnetic field C emitted in the reception zone.

As an example, the power corresponds to the Poynting vector, the square of the electrical component or the square of the magnetic component of the electromagnetic field emitted by the second unit 30.

Advantageously, the second end 33B coincides with a line 58 along which the power of the electromagnetic field emitted by the second communication unit 30 is the same. In the present description, this line 58 is called "iso-power line 58".

For example, the iso-power line 58 defines a predefined electromagnetic power, denoted $\pi_1$. The predefined power $\pi_1$ is inclusively between 50 dBA/m and 54 dBA/m. The unit dBA/m corresponds to the value of the magnetic field in Amperes per meter, on a scale in decibels.

For example, the predefined power $\pi_1$ is equal to 52 dBA/m.

The second end 33B of the communication zone 32 is located at a non-zero distance H from the first end 32A in the vertical direction Z.

The second end 33 for example has a concave shape.

Furthermore, the position of the second end 33B corresponds to the maximum of the curve forming the iso-power line 58.

As a result, the height H is the distance between the plane P1 and the maximum of the curve formed by the iso-power line 58.

Therefore, in the communication zone 32, the power of the electromagnetic field, denoted $\pi$, emitted by the second communication unit 30 is greater than or equal to the power $\pi_1$ defined by the iso-power line 58. Furthermore, above the second end 33B in the vertical direction Z, the power $\pi$ emitted by the second communication unit 32C is strictly less than the power $\pi_1$.

Furthermore, the width of the communication zone 32 is delimited by the waveguide 31.

The waveguide 31 guides the waves generated by the second communication unit 30 in the guide channel 56 so that the height H of the communication zone 32 is strictly greater than a reference dimension HR.

The reference dimension HR is measured in the vertical direction Z. The reference dimension is therefore referred to hereinafter as "reference height HR".

The reference height HR corresponds to the height of the communication zone when the storage device 20 is without waveguides 31.

In order to differentiate between the communication zone 32 of a storage device 20 comprising a waveguide 31 and that of a communication device 20 not comprising a waveguide 31, the communication zone of a storage device 20 not comprising a waveguide 31 is denoted "communication zone 32'". The communication zone 32' is delimited on the one hand by the plane P1 and an iso-power line 58'.

The iso-power line 58' is similar to the iso-power line 58 of a storage device 20 comprising a waveguide 31. The iso-power line 58' is therefore a line along which the power of the electromagnetic field generated by the second communication unit 30 is the same and equal to the reference power ill.

The height HR is therefore the distance between the plane P1 and the maximum of the curve formed by an iso-power line 58'.

The height H of the communication zone 32 is strictly greater than the reference height HR.

For example, the height H of the communication zone 32 is greater than or equal to 105% of the reference height HR, preferably greater than or equal to 115%, or preferably greater than or equal to 120%. Advantageously, the height of the communication zone 32 is less than or equal to 130% of the reference value HR.

For example, the reference height HR is inclusively between 75 mm and 90 mm.

In the case at hand, the reference height is equal to 86 mm. For example, the height H of the communication zone is equal to 109 mm.

In other words, the height H measured from the second communication unit 30 to which each first communication unit 15 is read by the second communication unit 30 is greater than that of a storage device 20 not comprising a waveguide 31.

It is therefore possible to store the elements 12 vertically and perpendicular to the second communication units 30, and to read the first communication units 15 borne by these elements 12 reliably.

Furthermore, by using the second communication units 30, it is possible to read, with no reading hole, each associated first communication unit 15 along the transverse X and longitudinal Y directions.

The storage installation 20 comprising the storage device makes it possible to meet the various requirements defined in the health field regarding bag storage. Indeed, the installation 10 offers flexibility in the positioning of the elements 12, that is to say the bags, while ensuring reliable reading of all of the RFID tags 15 positioned on these bags 12.

It should be noted that, in each of the described embodiments, the waveguide 31 is able to concentrate a magnetic field emitted by each associated second communication unit 30.

In this sense, each waveguide 31 is a magnetic field concentrator, the two terms "waveguide" and "magnetic field concentrator" thus being able to be used interchangeably to designate the waveguide 31.

In particular, the waveguide 31 is able to concentrate a magnetic field emitted by each associated second communication unit 30 so that the dimension H of each communication zone 32 measured from this associated second communication unit 30 along a predetermined direction is strictly greater than the reference dimension HR.

More specifically, the waveguide 31 is able to concentrate the magnetic field emitted by each associated second communication unit 30 along the vertical direction Z forming the predetermined direction.

In other words, the waveguide 31 makes it possible to increase the density of the magnetic field emitted by each associated second communication unit 30 in the predetermined direction Z.

Thus, the waveguide 31 is configured to constrain the shape of the loops of the magnetic field emitted by the associated second communication unit 30 in the predetermined direction.

The effect of the waveguide 31 on the electric field is not among the sought effects.

Therefore, the first and second plates 52, 54 of the waveguide 31 as previously described form magnetic field concentrating elements configured to concentrate the magnetic field emitted by each associated second communication unit 30 in the vertical direction Z.

Thus, the channel 56 defined between the first plate 52 and the second plate 54 is configured to concentrate the magnetic field.

The storage device 20 according to the invention differs from the known storage devices in that it comprises a waveguide 31 suitable for concentrating the magnetic field emitted by second concentrating units tuned to a frequency of 13.56 MHz±7 kHz.

The known storage devices do not comprise waveguides suitable for concentrating a magnetic field so as to increase the size of a communication zone.

In particular, second communication units suitable for emitting waves at a frequency of 915 MHz, as is the case in the state of the art, are not suitable for working with the waveguides 31 according to the invention. Indeed, such a frequency does not make it possible to obtain a sufficient dimension H of the communication zone along the predetermined direction.

Furthermore, a second communication unit transmitting waves at a frequency of 915 MHz is not suitable for communicating with first communication units that resonate at the frequency of 13.56 MHz±7 kHz as is the case in the invention. Indeed, the first communication units resonating at the frequency of 13.56 MHz±7 kHz are only sensitive to a signal of 13.56 MHz emitted by the second communication unit.

Furthermore, some storage devices of the state of the art comprise drawers forming Faraday cages, suitable for receiving first communication units. This type of drawer does not, unlike the present invention, make it possible to concentrate the magnetic field emitted by a second communication unit so as to increase a dimension of a communication zone.

The invention claimed is:

1. An element storage device, each element comprising a first wireless communication unit, the storage device comprising:
   a receiving support for receiving the elements,
   a second wireless communication unit able to generate waves, the second wireless communication unit being able to communicate with each first wireless communication unit according to a communication protocol, a communication zone also being defined as being a three-dimensional zone in which the second wireless communication unit is able to communicate with each first wireless communication unit when each first wireless communication unit is located in the communication zone, the second wireless communication unit not being able to communicate with at least one first wireless communication unit when the first wireless communication unit is located outside the communication zone,
   a waveguide able to guide the waves generated by the second wireless communication unit so that a dimension of the communication zone measured from the second wireless communication unit along a predetermined direction is strictly greater than a reference dimension, the reference dimension being equal to the dimension of the communication zone measured from the second wireless communication unit along the predetermined direction when the storage device is without waveguides.

2. The element storage device according to claim 1, wherein the waves generated by the second wireless communication unit are electromagnetic waves including a magnetic field, the waveguide being a magnetic field concentrator suitable for concentrating the magnetic field generated by the second wireless communication unit.

3. The element storage device according to claim 2, wherein the waveguide is able to guide the waves generated by the second wireless communication unit in the predetermined direction.

4. The element storage device according to claim 2, wherein the dimension of the communication zone verifies one of the following properties:
   the dimension of the communication zone is greater than or equal to 105% of the reference dimension,
   the dimension of the communication zone is greater than or equal to 120% of the reference dimension, and
   the dimension of the communication zone is less than or equal to 130% of the reference dimension.

5. The element storage device according to claim 1, wherein the waveguide is able to guide the waves generated by the second wireless communication unit in the predetermined direction.

6. The element storage device according to claim 5, wherein the dimension of the communication zone verifies one of the following properties:
   the dimension of the communication zone is greater than or equal to 105% of the reference dimension,
   the dimension of the communication zone is greater than or equal to 120% of the reference dimension, and
   the dimension of the communication zone is less than or equal to 130% of the reference dimension.

7. The element storage device according to claim 1, wherein the dimension of the communication zone verifies one of the following properties:
   the dimension of the communication zone is greater than or equal to 105% of the reference dimension,
   the dimension of the communication zone is greater than or equal to 120% of the reference dimension, and
   the dimension of the communication zone is less than or equal to 130% of the reference dimension.

8. The element storage device according to claim 1, wherein the waveguide comprises guide elements configured to guide the waves generated by the second wireless communication unit in the predetermined direction.

9. The element storage device according to claim 8, wherein the waveguide comprises two plates of equal sizes, parallel to one another, the two plates delimiting a guide channel between them for guiding the waves generated by the second wireless communication unit in the predetermined direction.

10. The element storage device according to claim 1, wherein the waveguide is made from metal.

11. The element storage device according to claim 10, wherein the metal is aluminum.

12. The element storage device according to claim 1, wherein the reference dimension is equal to 86 millimeters.

13. The element storage device according to claim 1, wherein the elements of the plurality of elements are containers of biological products, medications or therapeutic preparations and each first wireless communication unit is a radiofrequency identification tag comprising a memory that is able to store a datum relative to the container bearing this first wireless communication unit.

14. An installation for storing elements comprising:
an enclosure comprising an inner compartment, and
a storage device according to claim 1, comprising a plurality of elements each bearing a first wireless communication unit, the second wireless communication unit being intended to communicate with each first wireless communication unit according to a communication protocol,
the storage device being arranged in the inner compartment.

15. The element storage device according to claim 1, wherein the first wireless communication unit is a radiofrequency identification tag and comprises at least one antenna.

16. The element storage device according to claim 15, wherein the at least one antenna is planar and in the shape of an eight.

17. The element storage device according to claim 15, wherein the radiofrequency identification tag comprises a plurality of antennas having overlap zones relative to one another.

18. A communication method between at least a first wireless communication unit and a second wireless communication unit implemented in an element storage device, each element comprising a first wireless communication unit, the element storage device comprising:
a receiving support for receiving the elements,
a second wireless communication unit able to generate waves, the second wireless communication unit being able to communicate with each first wireless communication unit according to a communication protocol, a communication zone also being defined as being a three-dimensional zone in which the second wireless communication unit is able to communicate with each first wireless communication unit when each first wireless communication unit is located in the communication zone, the second wireless communication unit not being able to communicate with at least one first wireless communication unit when the first wireless communication unit is located outside the communication zone,
a waveguide able to guide the waves generated by the second wireless communication unit so that a dimension of the communication zone measured from the second wireless communication unit along a predetermined direction is strictly greater than a reference dimension, the reference dimension being equal to the dimension of the communication zone measured from the second wireless communication unit along the predetermined direction when the storage device is without waveguides,
the method comprising a step for transmitting waves by means of the second wireless communication unit,
during the step for transmitting, the dimension of the communication zone measured from the second wireless communication unit along the predetermined direction is greater than or equal to the reference dimension.

19. The communication method according to claim 18, wherein the waveguide comprises guide elements configured to guide the waves generated by the second wireless communication unit in the predetermined direction, the guide elements comprising two plates of equal dimensions, parallel to one another delimiting a channel between them,
during the step transmitting waves by the second wireless communication unit, the second wireless communication unit transmits electromagnetic waves comprising a magnetic field and the two plates concentrate, in the channel, the magnetic field emitted by the second wireless communication unit.

20. The installation for storing elements according to claim 18, wherein the enclosure is a refrigerating enclosure.

* * * * *